United States Patent [19]
Elongo et al.

[11] Patent Number: 4,935,522
[45] Date of Patent: * Jun. 19, 1990

[54] PROCESS FOR PRODUCING ETHYL 2-[4'-(6"-CHLORO-2"-BENZOXAZOLYLOXY)PHENOXY]PROPIONATE

[75] Inventors: Varadaraj Elongo; Kenneth G. Davenport, both of Corpus Christi, Tex.

[73] Assignee: Hoechst Celanese Corporation, Somerville, N.J.

[*] Notice: The portion of the term of this patent subsequent to Mar. 13, 2007 has been disclaimed.

[21] Appl. No.: 170,797

[22] Filed: Mar. 21, 1988

[51] Int. Cl.$^5$ .................................... C07D 263/58
[52] U.S. Cl. ............................ 548/221; 560/144
[58] Field of Search ......................... 548/221

[56] References Cited

U.S. PATENT DOCUMENTS

| | | | |
|---|---|---|---|
| 2,068,905 | 1/1937 | Bruson | 562/471 |
| 4,130,413 | 12/1978 | Handte | 548/221 |
| 4,153,803 | 5/1979 | Thiele et al. | 562/471 |
| 4,173,709 | 11/1979 | Metivier et al. | 562/471 |
| 4,528,394 | 7/1985 | Otterbacher | 560/61 |
| 4,532,346 | 7/1985 | Rehn | 562/471 |
| 4,537,984 | 8/1985 | Hashiba et al. | 562/471 |
| 4,547,583 | 10/1985 | Nestler | 562/471 |
| 4,661,505 | 4/1987 | Marshall et al. | 562/464 |
| 4,665,212 | 5/1987 | Makino et al. | 562/471 |
| 4,747,865 | 5/1988 | Shiokawa | 548/221 |

FOREIGN PATENT DOCUMENTS

| | | |
|---|---|---|
| 0082413 | 6/1983 | European Pat. Off. . |
| 178929 | 4/1986 | European Pat. Off. . |
| 2003430 | 1/1970 | Fed. Rep. of Germany . |
| 55-79344 | 6/1980 | Japan . |
| 62-178543 | 8/1987 | Japan . |
| 1599121 | 9/1981 | United Kingdom . |

OTHER PUBLICATIONS

Ogata, Y., (1978), J. Org. Chem., 43(12), pp. 2417-2419.
McKillop, A., (1987), Tetrahedron, 43(8), pp. 1753-1758.
Chemical Abstracts, 93:7777n, (1980).
Method of Formation of the Ether Linkage—Feuer et al.
Organic Reactions, vol. IX, pp. 73-106.
Chemical Abstracts, CA 108(1):5692K.
CA 77(13):88107p.

Primary Examiner—Donald G. Daus
Attorney, Agent, or Firm—D. R. Cassady

[57] ABSTRACT

A method for producing ethyl 2-[4'-(6"-chloro-2"-benzoxazolyloxy)phenoxy]propanoate by reacting a hydroxyaromatic ketone derivative with a 2-substituted propanoic ester under basic conditions and thereafter oxidizing the intermediate with subsequent hydrolysis and reaction with 2,6-dichlorobenzoxazole.

15 Claims, No Drawings

PROCESS FOR PRODUCING ETHYL 2-[4'-(6''-CHLORO-2''-BENZOXAZOLYLOXY)-PHENOXY]PROPIONATE

BACKGROUND OF THE INVENTION

The present invention relates to a method for the synthesis of ethyl 2-[4'-(6''-chloro-2''-benzoxazolyloxy)-phenoxy]propanoate. This compound is useful as a herbicide.

It is known in the art to produce herbicidal agents which are heterocyclic substituted 2-aryloxyphenoxy)alkanoic acids. Within this context aryl includes benzthiazolyl, benzoxazolyl, benzpyrozolyl, etc., derivatives. Such may be described by the generalized formula:

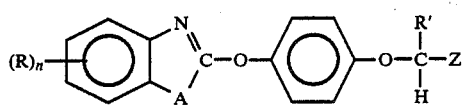

in which $(R)_n$ is hydrogen, halogen, $CF_3$, $NO_2$, CN, alkyl, alkoxy or alkylthio, A is O, S, NH, or N-alkyl R' is hydrogen or alkyl and Z is a carboxylic acid, carboxylic ester, thiol ester, carbamide, carbohydrazide, thioamide, nitrile, hydroxymethyl, acyloxymethyl, carbamoylmethyl, or a sulfonyloxymethyl group. The most preferred compound is ethyl 2-[4'-(6''-chloro-2''-benzoxazolyloxy)-phenoxy]propanoate and has the structure:

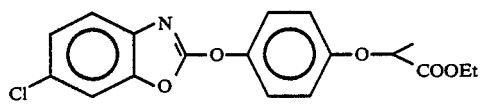

(I)

The compounds of the formula I possess an asymmetric carbon center and therefore occur as pure enantiomers or as a mixture thereof. These and other compounds are more fully described in U.S. Pat. Nos. 4,589,908; 4,130,413; and 4,564,682; and German Patents DE 3502266, 3430215, 3418168, 3311285, 3236730, and 3036075, and European Patent Applications 148119 and 157225, all of which are incorporated herein by reference. One method for the production of these herbicides uses an intermediate which is a 2-(4-hydroxyphenoxy)alkanoic acid ester of the formula:

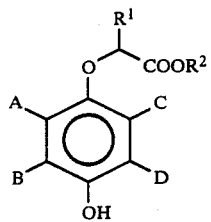

(II)

wherein $R^1$ is H, phenyl or $C_1$ to $C_{18}$ alkyl, preferably $C_1$ to $C_4$ alkyl; and wherein $R_2$ is $C_1$ to $C_8$ alkyl, preferably $C_1$ to $C_4$ alkyl or aryl such as phenyl or naphthyl which may be substituted or unsubstituted; and wherein A, B, C and D are independently H, S, O, N, X, $C_1$ to $C_{18}$ alkyl, or $C_6$ to $C_{10}$ aryl; and X is F, Cl, Br, I or a sulfonic ester.

Prior art processes for producing these intermediate compounds have employed hydroquinone and other compounds as starting materials. Such processes are discussed at length in U.S. Pat. Nos. 3,600,437; 4,532,346; 4,547,583; and British Patent 1,591,063. U.S. Pat. No. 4,665,212 teaches condensed hydroquinone or hydroquinone salts with certain aromatic sulfonyl containing acids, esters and salts. U.S. Pat. 4,511,731 teaches the preparation of certain propanoate monoethers of hydroquinone via sequential alkylation and oxidation of hydroxystyrene. While such processes are effective for producing herbicide precursors, they are economically disadvantageous since the selectivity and rate of conversion, and hence the yield, is relatively low; on the order of about 10%. U.S. Pat. No. 4,528,394 describes a method which improves upon this yield by using a benzaldehyde precursor such that the yield is increased to about 50%. However, this system is disadvantageous because of the vigorous reaction conditions required and undesired side reactions which occur such as the self-condensation of the benzaldehyde. These may also undergo undesired oxidation to carboxylic acids under Baeyer-Villiger conditions. The present invention improves on these methods by preparing herbicides using intermediates derived from certain ketones and conducting a Baeyer-Villiger oxidation thereon. The intermediates are prepared in a stepwise fashion and several advantages are thereby noted. These include a higher yield, perhaps in the 80-95% range, easier purification of the intermediates and less vigorous reaction conditions. The invention therefore provides a process for obtaining the foregoing herbicidal compound from a hydroxyaromatic ketone and 2,6-dichlorobenzoxazole.

SUMMARY OF THE INVENTION

The invention provides a method for synthesizing ethyl 2-[4'-(6''-chloro-2''-benzoxazolyloxy)phenoxy]-propionate which comprises reacting a hydroxyaromatic ketone derivative of the formula

(III)

or a salt thereof; with a substituted ester of the formula

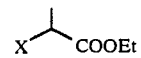

under basic conditions to thereby form ethyl 2-(4-acylphenoxy)propanoate (IV) of the formula

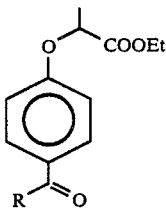

and then oxidizing the thusly formed ethyl 2-(4-acylphenoxy)propanoate (IV) with a peracid or peroxide to obtain an ethyl 2-(4-acyloxyphenoxy)propanoate (V) of the formula

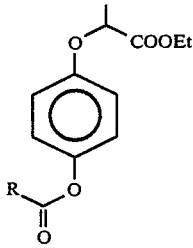

and then hydroylyzing or alcoholizing said ethyl 2-(4-acyloxyphenoxy)propanoate (V) to obtain ethyl 2-(4-hydroxyphenoxy)propanoate (VI) of the formula

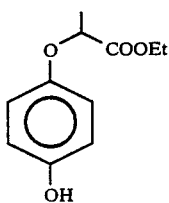

and then reacting the ethyl 2-(4-hydroxyphenoxy)-propanoate with 2,6-dichlorobenzoxazole to obtain ethyl 2-[4'-(6"-chloro-2"-benzoxazolyloxy)phenoxy]-propanoate wherein R is $C_1$ to $C_{18}$ alkyl or $C_6$ to $C_{10}$ aryl, preferably $C_1$ to $C_4$ alkyl, and most preferably methyl; and X is F, Cl, Br, I or a sulfonic ester.

DETAILED DESCRIPTION OF THE PREFERRED EMBODIMENT

In the production of the herbicides of this invention, one begins with a hydroxyaromatic ketone and reacts it with one of the aforesaid substituted esters under basic conditions. This reaction product is then subjected to a Baeyer-Villiger oxidation with peracetic acid being the preferred reagent. The resulting product is then hydrolyzed or alcoholized to the 2-(4-hydroxyphenoxy)alkanoic acid ethyl ester. This compound is then reacted with 2,6-dichlorobenzoxazole to obtain the desired herbicidal compound. The reaction sequence may be generalized as:

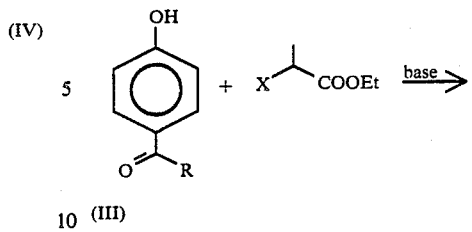

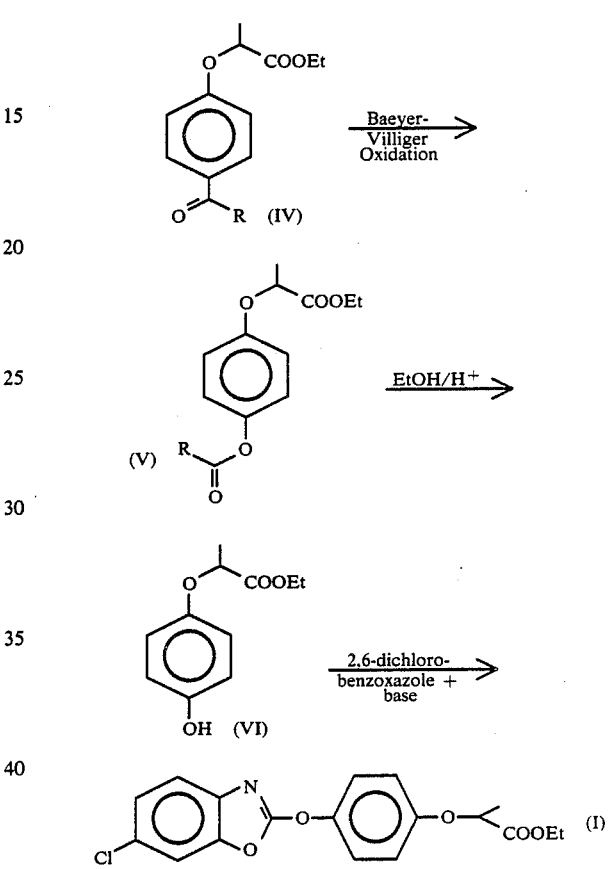

The compounds of formulae I, IV, V, VI possess an asymmetric carbon center and can therefore occur as pure enantiomers (optically active) or racemic as mixtures of enantiomers. An important feature of this invention is to begin the synthesis with an aromatic ketone which is specifically a 4-hydroxyphenyl ketone compound (III). The most preferred ketone being 4-hydroxyacetophenone, as well as its sodium and potassium salts. These hydroxyphenones are then reacted with one of the aforesaid X-substituted esters which may be either racemic or optically active. Preferred esters are halogen substituted propanoates such as ethyl 2-chloropropanoates, ethyl 2-bromopropanoate, ethyl 2-[(methylsulfonyl)oxy]propanoate, and ethyl 2-[(toluylsulfonyl)oxy]propanoate. This reaction proceeds by the Williamson's ether synthesis process which is well-known to the skilled artisan. The reaction may take place by refluxing the hydroxyaromatic ketone with the ester in a solvent such as dimethylformamide under basic conditions. The basic conditions may be provided either by direct use of a base such as an alkali metal or alkaline earth metal hydroxide or carbonate, amines or a hydride such as potassium hydride.

Alternatively, within the meaning of this invention, the basic media may be provided by using one of the aforesaid salt forms of the hydroxyphenone, such as 4-hydroxyacetopheone sodium or potassium salt. Alternative solvents for the refluxing reaction non-exclusively include polar protic solvents, e.g., water or alcohol, or polar aprotic solvents, e.g., ketones, ether, nitriles, and sulfoxides. The reaction may take place at from about 0.1 to about 72 hours, or more preferably form about 1 to about 48 hours at a temperature of from about 0° C. to about 300° C. or more preferably from about 25° C. to about 200° C. The reaction product at this juncture is ethyl 2-(4-acylphenoxy)propanoate (IV). In one preferred embodiment the foregoing reactants are 4-hydroxyacetophenone potassium salt and ethyl 2-bromopropanoate with refluxing in dimethylformamide. Alternatively, the reactants are 4-hydroxyacetopheone, potassium hydroxide and ethyl 2-chloropropanoate with refluxing in dimethylformamide. Therefore the preferred ethyl 2-(4-acylphenoxy)-propanoate (IV) produced is ethyl 2-(4'-acetylpheonxy)propanoate. This is then oxidized by the Baeyer-Villiger oxidation process which is also well known to the skilled artisan per se. The oxidation is conducted by refluxing the ethyl 2-(4-acyphenoxy)propanoate (IV) with a peracid or perester in a suitable solvent. The most preferred oxidizing agent is peracetic acid. Others non-exclusively include hydrogen peroxide, alkyl peroxides, chloroperacetic acid, peroxybenzoic acid, and meta-chloroperoxybenzoic acid and trifluoroperoxyacetic acid. One preferred solvent for the refluxing is acetic acid. Alternative solvents for the refluxing reaction on-exclusively include water, alcohols, esters, ethers, halogenated hydrocarbons and carboxylic acids. The reaction may take place at from about 0.01 to about 24 hours, or more preferably from about 0.1 to about 10 hours at a temperature of from about 0° C. to about 100° C. or more preferably from about 25° C. to about 75° C. The reaction may take place at either elevated or reduced pressures, however, preferably it is performed at reduced pressure to remove heat generated during the reaction.

The reaction product of this juncture is ethyl 2-(4-acyloxyphenoxy)propanoate (V) which in the most preferred embodiment is ethyl 2-(4-acetoxyphenoxy)-propanoate. This latter component is then hydrolyzed or alcoholized. The alcoholysis may be conducted by contacting with alcohols under acidic conditions and elevated temperatures for a period of time sufficient to permit the reaction to approach completion. The amount of alcohol used may be, for example, about 0.5 to about 1,000 mol equivalents; preferably about 1 to about 100 mol equivalents based on the ester being alcoholized. The acids which may be employed for this purpose are organic acids such as methanesulfonic acid, para-toluenesulfonic acid, mineral acids such as sulfuric, hydrochloric and phosphoric acids, and acidic ion exchange resins. In some instances, it may be desirable to employ a combination of alcohol and water to achieve a measure of solvolysis. The hydrolysis may be conducted by refluxing with $R^3OH/H+$ wherein $R^3$ is phenyl or C1 to C16 alkyl. Preferably hydrolysis is conducted with ethyl alcohol. Most preferable, hydrolysis is also conducted with a catalytic amount of an acid such as HCl.

Alcoholysis may take place at a from about 0.1 to about 10 hours, or more preferably from about 0.5 to about 4 hours at a temperature of from about 20° C. to about 200° C. or more preferably from about 60° C. to about 140° C. The reaction is conducted with an anticipated conversion of from about 90% to about 99% with a selectivity of from about 90% to about 98%. The solvolysis product is a ethyl 2-(4-hydroxyphenoxy)-propanoate (VI).

Lastly, the ethyl 2-(4-hydroxyphenoxy)propanoate is reacted with 2,6-dichlorobenzoxazole to produce ethyl 2-[4-(6"-chloro-2"-benzoxazolyloxy)phenoxy]propanoate (I). The reaction may take place at from about 0.1 to about 24 hours, or more preferably from about 0.5 to about 10 hours at a temperature of from about 0° C. to about 350° C. or more preferably from about 25° C. to about 200° C. The reaction is preferably carried out in aprotic solvents such as hydrocarbons, ketones, ethers, nitriles, amides, and sulfides. In the preferred embodiment this last reaction takes place in the presence of a base such as those listed heretofore. The following non-limiting examples serve to illustrate the invention.

EXAMPLE 1

To a solution of the potassium salt of 4-hydroxyacetophenone (25.0 g, 0.14 mol) in DMF (100 ml) is added ethyl 2-chloropropanoate (27.3 g, 0.20 mol) over 30 minutes and stirred at 85°–90° C. for 3 under nitrogen. The reaction is filtered to remove KCl and the filtrate is concentrated under reduced pressure to remove DMF and the product is analyzed by GLC. The product is dissolved ine thyl acetate (300 mL) and extracted with 2N NaOH (2x 100 mL) and water (100 mL). The organic phase is dried and concentrated to give pure ethyl 2-(4-acetylphenoxy)-propanoate (30 g) (yield 75%); m.p. 49.6° C.; IR (KBr) 1747.7 (vs), 1669.8 (vs); $^1H$ NMR (CHCl$_3$) delta 1.18 (t, J=7.2 Hz, 3H), 1.58 (d, J=6.8 Hz, 3H), 2.46 (s, 3H), 4.15 (q, J=7.2, 2H), 4.77 (q, J=6.8, $^1H$), 6.83 and 7.84 (dd, J=9.0 Hz, 4H).

EXAMPLE 2

A solution of the potassium salt of 4-hydroxyacetophenone (17.6 g, 0.1 mol) in DMF (50 mL) is added to a solution of ethyl L-2-[(methylsulfonyl)oxy]-propanoate (21.5 g, 0.11 mol) in DMF (40 mL) over 15 minutes at 80° C. and stirred at 80° C. for 2 hours. to the reaction is added ethyl acetate (100 mL) and filtered. The filtrate is concentrated under reduced pressure whereupon the product is analyzed by GLC. The product is dissolved in ethyl acetate (250 mL) and extracted with saturated sodium bicarbonate solution (2×100 mL) and water (2×60 mL). The organic phase is dried and concentrated to give ethyl 2-(4-acetylphenoxy)-propanoate (20.2 g).

EXAMPLE 3

To a solution of ethyl 2-(4-acetylphenoxy)propanoate (5.01 g, 21.0 mmol) in equilibrium with acetic acid (50 mL) is added peracetic acid (16%, 15.61 g, 33.0 mmol) dropwise over 30 minutes at 58° C. and 60 mm HgA until all is added. The reaction mixture is refluxed at a temperature of 48°–54° C. and a vacuum of 55–60 mm Hg. The reaction continues for 8 hours, is cooled to room temperature and concentrated under reduced pressure to remove the acetic acid from which ethyl 2-(4-acetoxyphenyl)propanoate (5.34 g) is obtained. (yield 90%): b.p. 120°–122° C. at 0.06 mm HgA, IR (neat) 1752 (vs); $^1h$ NMR (CDCl$_3$) delta 1.22 (t, J=7.0 Hz, 3H), 1.57 (d, J=6.8 Hz, 3H), 2.23 (s, 3H), 4.18 (q, J=7.0 Hz, 2H), 4.70 (q, J=6.8 hz, $^1H$), 6.85 and 6.96 (dd, J=9.4 hz, 4H).

EXAMPLE 4

Ethyl 2-(4-acetylphenoxy)propanoate (5.01 g, 21.0 mmol) is dissolved in acetic acid (10 ML) and Amberlyst-15(R) (0.24 g) added. Hydrogen peroxide (70%), 1.58 g, 33.0 mmol is then charged dropwise over 30 minutes to the reaction. The reaction is refluxed for 8 hours at 45°–60° C. and 57–60 mm HgA whereupon the reaction is analyzed by GLC. The reaction is cooled to room temperature and concentrated under reduced pressure to give ethyl 2-(4-acetoxyphenoxy)propanoate (4.72 g) (yield 88.3%).

EXAMPLE 5

To a solution of ethyl 2-(4'-acetylphenoxy)propanoate (5.07 g, 21.5 mmols) in acetic acid (25 mL) is added peracetic acid (35%, 7.4 g, 33.9 mmols) dropwise over 30 minutes. The reaction mixture is stirred at 55°–60° C. and 60 mm HgA for 5 hours. Acetic acid and residual peracetic acid are removed under high vacuum. The solution is kugelrohr distilled to give a product which contains ethyl 2-(4-acetoxyphenoxy)propanoate (5.41 g) )yield 89%).

EXAMPLE 6

Ethyl 2-(4-acetoxyphenoxy)propionate (5.01 g, 19.9 mmol) is hydrolyzed by refluxing for 2 hours at 80° C. with ethanol (40 mL) and concentrated HCl (36%, 2 drops). The reaction product is concentrated under reduced pressure to obtain ethyl 2-(4-hydroxyphenoxy)propionate (3.8 g) (yield 93%), $^1$NMR (CHCl$_3$) delta 1.25 (t, J=7.0 Hz, 3H), 1.62 (d, J=6.8 Hz, 3H), 4.21 (q, J=7.0 Hz, 2H), 4.65 (q, J=6.8 Hz, 1H), 6.74 (M, 4H).

EXAMPLE 7

To a solution of ethyl 2-(4-hydroxyphenoxy)propionate (2.0 g, 9.8 mmol) in acetonitrile (25 mL) is added potassium carbonate (2.0 g), 14.5 mmol) and refluxed for an hour. The reaction mixture is cooled to room temperature and 2,6-dichlorobenzoazole (1.8 g, 10.2 mmol) is added. The reaction is refluxed for 4 hours and concentrated to dryness. To the reaction is added acetonitrile (50 mL), refluxed for 2 hours, and the hot mixture is filtered. The filtrate is concentrated to about 25 mL and cooled to afford ethyl 2-[4'-6"-chloro-2"-benzoxazolyloxy)phenoxy]propanoate (2.9 g) (yield 85%).

What is claimed is:

1. A method for producing ethyl 2-[4'-(6"-chloro-2"-benzoxazolyloxy)phenoxy]propionate which comprises reacting a hydroxyaromatic ketone derivative (III) of the formula

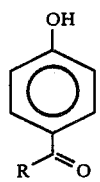

or a salt thereof; with a substituted ester of the formula

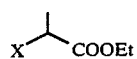

under basic conditions to thereby form ethyl 2-(4-acylphenoxy)propanoate (IV), of the formula

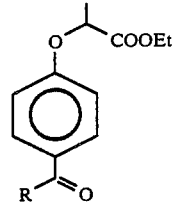

and then oxidizing the thusly formed ethyl 2-(4-acrylphenoxy)propanoate (IV) with a peracid or peroxide to obtain an ethyl 2-(4-acyloxyphenoxy)propanoate (V) of the formula

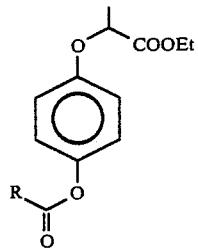

and then hydrolyzing or alcoholizing said ethyl 2-(4-acyloxyphenoxy)propanoate (V) to obtain ethyl 2-(4-hydroxyphenoxy)propanoate (VI) of the formula

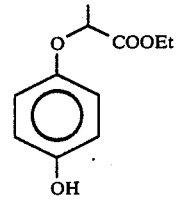

and then reacting the ethyl 2-(4-hydroxyphenoxy)propanoate (VI) with 2,6-dichlorobenzozazole to obtain ethyl 2-[4'-(6"-chloro-2"-beznoxazolyloxy)phenoxy]propanoate; wherein R is $C_1$ to $C_{18}$ alkyl or $C_6$ to $C_{10}$ aryl; and X is F, Cl, Br, I or a sulfonic ester.

2. The method of claim 1 wherein R is $CH_3$.

3. The method of claim 1 wherein said hydroxyaromatic ketone is a potassium or sodium salt.

4. The method of claim 1 wherein x is bromine, chlorine, mesylate or tosylate.

5. The method of claim 1 wherein said base is sodium hydroxide or potassium carbonate.

6. The method of claim 1 wherein said base is selected from the group consisting of alkali metal and alkaline earth metal hydroxides or carbonates, amines and hydrides.

7. The method of claim 1 wherein said oxidation is conducted with peracetic acid.

8. The method of claim 1 wherein oxidation is conducted with a compound selected from the group consisting of chloroperacetic acid, peroxybenzoic acid, trifluoroperoxyacetic acid, meta-chloroperoxybenzoic acid, an alkyl peroxide or hydrogen peroxide.

9. The method of claim 1 wherein said alcoholysis is conducted with $R^3OH/H+$ wherein $R^3$ is phenyl or C1-C16 alkyl.

10. The method of claim 9 wherein said alcoholysis is conducted with a catalytic amount of an acid.

11. The method of claim 10 wherein said acid is HCl.

12. The method of claim 1 wherein said hydrolysis is conducted with ethanol.

13. The method of claim 1 wherein said hydroxyaromatic ketone is 4-hydroxyacetophenone.

14. The method of claim 13 wherein X is bromine, chlorine, mesylate or tosylate and said oxidation is conducted with peracetic acid and asid hydrolysis is conducted with ethanol.

15. The method of claim 1 wherein said 2-substituted propanoic acid ester is an optically active compound.

* * * * *